(12) United States Patent
Yajima (10) Patent No.: US 8,653,473 B2
(45) Date of Patent: Feb. 18, 2014

(54) CHARGED PARTICLE BEAM IRRADIATION DEVICE

(71) Applicant: Sumitomo Heavy Industries, Ltd., Tokyo (JP)

(72) Inventor: Satoru Yajima, Niihama (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 13/741,856

(22) Filed: Jan. 15, 2013

(65) Prior Publication Data

US 2013/0184512 A1 Jul. 18, 2013

Related U.S. Application Data

(63) Continuation of application No. PCT/JP2011/066256, filed on Jul. 15, 2011.

(30) Foreign Application Priority Data

Jul. 28, 2010 (JP) .................................. 2010-169215

(51) Int. Cl.
*G21K 5/04* (2006.01)

(52) U.S. Cl.
USPC ................ 250/396 R; 250/492.1; 250/492.3; 600/1; 315/500

(58) Field of Classification Search
USPC ........ 250/396 R, 397, 492.1, 492.3; 315/500, 315/501, 502, 503, 504, 505; 600/1
See application file for complete search history.

(56) References Cited

U.S. PATENT DOCUMENTS

| 2004/0111134 | A1* | 6/2004 | Muramatsu et al. ............. 607/88 |
| 2010/0192303 | A1* | 8/2010 | Miller et al. ....................... 5/622 |
| 2010/0230617 | A1* | 9/2010 | Gall .......................... 250/492.21 |

FOREIGN PATENT DOCUMENTS

| DE | 102007032025 A1 | 12/2008 |
| JP | 07-255867 A | 10/1995 |
| JP | 09-192244 A | 7/1997 |
| JP | 10-326699 A | 12/1998 |
| JP | 2001-346893 A | 12/2001 |
| JP | 2009-515671 A | 4/2009 |
| JP | 2010-125012 A | 6/2010 |

OTHER PUBLICATIONS

International Preliminary Report on Patentability dated Mar. 12, 2013 corresponding to International Patent No. PCT/JP2011/066256.
International Search Report dated Aug. 9, 2011 corresponding to International Patent Application No. PCT/JP2011/066256.

* cited by examiner

*Primary Examiner* — Nicole Ippolito
(74) *Attorney, Agent, or Firm* — Squire Sanders (US) LLP (57) ABSTRACT

A charged particle beam irradiation device includes a particle accelerator that accelerates charged particles and ejects a charged particle beam, a cylindrical outer shell part that is capable of rotating around a rotating axis, an irradiation unit that is capable of irradiating an irradiation target with the charged particle beam, the irradiation direction of which changes in accordance with the rotation of the outer shell part, and a beam transport line that transports the charged particle beam ejected from the particle accelerator to the irradiation unit. The particle accelerator and the beam transport line may be at least partially housed within the outer shell part.

8 Claims, 4 Drawing Sheets

CHARGED PARTICLE BEAM IRRADIATION DEVICE

INCORPORATION BY REFERENCE

Priority is claimed to Japanese Patent Application No. 2010-169215, filed Jul. 28, 2010, and International Patent Application No. PCT/JP2011/066256, the entire content of each of which is incorporated herein by reference.

BACKGROUND

1. Technical Field

The present invention relates to a charged particle beam irradiation device.

2. Description of the Related Art

Equipment is known in which a charged particle beam such as a proton beam is irradiated onto a patient to perform cancer treatment. This kind of equipment includes a particle accelerator (cyclotron or synchrotron) that accelerates ions generated by an ion source and ejects a charged particle beam, a rotatable irradiation unit (rotatable gantry) that irradiates the patient with the charged particle beam from an arbitrary direction and a beam transport line that transports the charged particle beam ejected from the particle accelerator to the irradiation unit.

In the equipment of the related art with this configuration, it is necessary to separately provide a space (chamber) for the particle accelerator being installed, a space for the beam transport line being installed and a space (chamber) for the rotatable gantry being installed. Further, in order to effectively perform treatment by using this equipment, a plurality of the rotatable gantries are generally provided for one particle accelerator. According to this, enlargement of the equipment occurs and then a large site area is necessary.

On the other hand, in order to enhance general versatility of this charged particle beam irradiation equipment, there is a demand that only one rotatable gantry be provided for one piece of equipment.

SUMMARY

According to an embodiment of the present invention, there is provided a charged particle beam irradiation device including: a particle accelerator that accelerates charged particles and ejects a charged particle beam; an outer shell part that is cylindrical and is capable of rotating around a rotating axis; an irradiation unit that is capable of irradiating an irradiation target with the charged particle beam, the irradiation direction of which changes in accordance with the rotation of the outer shell part; and a beam transport line that transports the charged particle beam ejected from the particle accelerator to the irradiation unit. The particle accelerator and the beam transport line may be at least partially housed within the outer shell part.

DETAILED DESCRIPTION

For example, as disclosed in the related art, a charged particle beam irradiation device is proposed in which a particle accelerator is provided within a rotatable gantry and the entire equipment is miniaturized. In this device, a dedicated particle accelerator is provided with one rotatable gantry. Naturally, it is possible to meet the demand that only one rotatable gantry be provided for one piece of equipment.

However, in the charged particle beam irradiation device of the related art in which a particle accelerator is provided within a rotatable gantry, there is a problem in construction efficiency as follows.

In the charged particle beam irradiation device of the related art, the respective elements, that is, a particle accelerator, a guide ring that rotates the entire device, a plurality of supporting members that support the particle accelerator in the guide ring, an irradiation unit of which the irradiation direction of the charged particle beam changes in accordance with the rotation of the guide ring and the like, are directly disposed in an installation chamber where the charged particle beam irradiation device is installed. That is to say, it is necessary to assemble the charged particle beam irradiation device at an installation location of the device while disposing the respective elements at predetermined positions in the location.

In this charged particle beam irradiation device, generally, there is a requirement to perform a performance test for checking whether or not a desired operation is performed. Therefore, it is necessary to perform the performance test after fabricating the respective elements at the installation location. As described above, in the charged particle beam irradiation device of the related art, since there are many processes to be performed at the installation location of the device, the installation process of the device, that is, a period from the start of the installation of the device at the installation location until the device is available, becomes excessively long, thereby becoming less efficient in construction.

It is desirable to provide a charged particle beam irradiation device for which the miniaturization of the entire device and the shortening of an installation process can be realized.

According to the charged particle beam irradiation device, the particle accelerator and the beam transport line may be at least partially housed within the cylindrical outer shell part. That is, since constituent elements necessary for the charged particle beam irradiation (the particle accelerator, the beam transport line and the irradiation unit) may be integrally assembled in the outer shell part, it is possible to miniaturize the entire device. Further, since the entire device is integrally assembled, it is possible to assemble the device at a factory or the like in advance. Therefore, when the device is assembled at a factory or the like in advance, it is possible to perform a performance test at the factory in advance and to shorten an installation process at an installation location. According to this, since the miniaturization of the device and the shortening of the installation process can be realized, it is possible to provide a greater range of choices for the installation location of the device, thereby enhancing general versatility. Furthermore, since the entire device is covered with the cylindrical outer shell part, the device can be lightweight while maintaining rigidity. Since the device can maintain rigidity, it is possible to prevent the device from being bent, for example, due to the weight of the particle accelerator or the like. Therefore, it is possible to prevent occurrence of isocenter (an intersection point between the rotating axis and the center line of the beam) displacement in the irradiation unit, thereby improving the irradiation accuracy of the charged particle beam.

The particle accelerator and the beam transport line may be held on an inner peripheral surface of the outer shell part. With this configuration, all constituent elements necessary for the charged particle beam irradiation (the particle accelerator, the beam transport line and the irradiation unit) may be disposed inside the outer shell part. Accordingly, it is possible to perform maintenance and adjustment on all constituent elements from the inside of the device, thereby improving maintainability.

The beam transport line may include an energy selection system that takes the charged particle beam having an energy range smaller than a predetermined energy range out of the charged particle beams having the predetermined energy range and the energy selection system may be housed within the outer shell part.

With this configuration, since the energy selection system does not protrude in the direction of the rotating axis of the outer shell part and the energy selection system is housed within the outer shell part, the entire device can be further miniaturized. In addition, when the charged particle beam irradiation device assembled at a factory or the like is transported to an installation location, the outer shell part may protect the energy selection system. Therefore, it is possible to prevent the energy selection system from being damaged when hit against another object.

The outer shell part may include a cutout portion, and the particle accelerator and the beam transport line may be at least partially exposed through the cutout portion.

With this configuration, it is possible to gain access to the particle accelerator and the beam transport line from the outside of the outer shell part, if necessary. Therefore, it is possible to perform maintenance from the outside of the outer shell part, thereby improving maintainability.

The beam transport line may include a deflection magnet, which determines an incident direction to the irradiation unit, at a finishing end of the beam transport line, and the particle accelerator and the deflection magnet may be respectively held at a position where the particle accelerator faces the deflection magnet around the rotating axis when seen from the view in parallel with the rotating axis.

With this configuration, it is possible to improve balance around the rotating axis of the outer shell part. In addition, the particle accelerator and the deflection magnet, which are held at a position where the particle accelerator faces the deflection magnet around the rotating axis, function as each other's counterweight. Therefore, it is not necessary to provide a new counterweight, thereby realizing the lightweight device.

The beam transport line may include a first line that extends from a starting end of the beam transport line connected to the particle accelerator along the rotating axis, a second line that extends from the finishing end of the beam transport line along the rotating axis and a third line that connects the first line and the second line.

With this configuration, it is possible to increase the deflection angle of the charged particle beam by the beam transport line. Accordingly, since a plurality of the energy selection systems are disposed in the beam transport line having a large deflection angle, it is possible to select energy of the charged particle beam in a stepwise manner, thereby selecting energy with high accuracy.

The deflection magnet may be held at a position of one end portion side in the direction along the rotating axis of the outer shell part, and the particle accelerator may be held at a position of the other end portion side in the direction along the rotating axis of the outer shell part. With this configuration, it is possible to improve balance of the outer shell part in the direction of the rotating axis, thereby reducing the bending of the direction of the rotating axis of the device.

The beam transport line may include a fourth line that extends from a starting end of the beam transport line connected to the particle accelerator in the direction perpendicular to the rotating axis and a fifth line that extends from the finishing end of the beam transport line along the rotating axis.

With this configuration, since the entire length of the beam transport line in the direction of the rotating axis can be shortened, it is possible to shorten the entire length of the outer shell part in the direction of the rotating axis. Consequently, a charged particle beam therapy device can be further miniaturized.

Hereinafter, a charged particle beam irradiation device according to a preferred embodiment of the present invention will be described with reference to drawings. In this embodiment, a case where the charged particle beam irradiation device is used for a proton therapy device will be described. The proton therapy device is used, for example, in the treatment of cancer. The proton therapy device is a device that irradiates a cancerous tumor in the body of a patient (irradiation target) with a proton beam (charged particle beam).

First Embodiment

Figure 1:
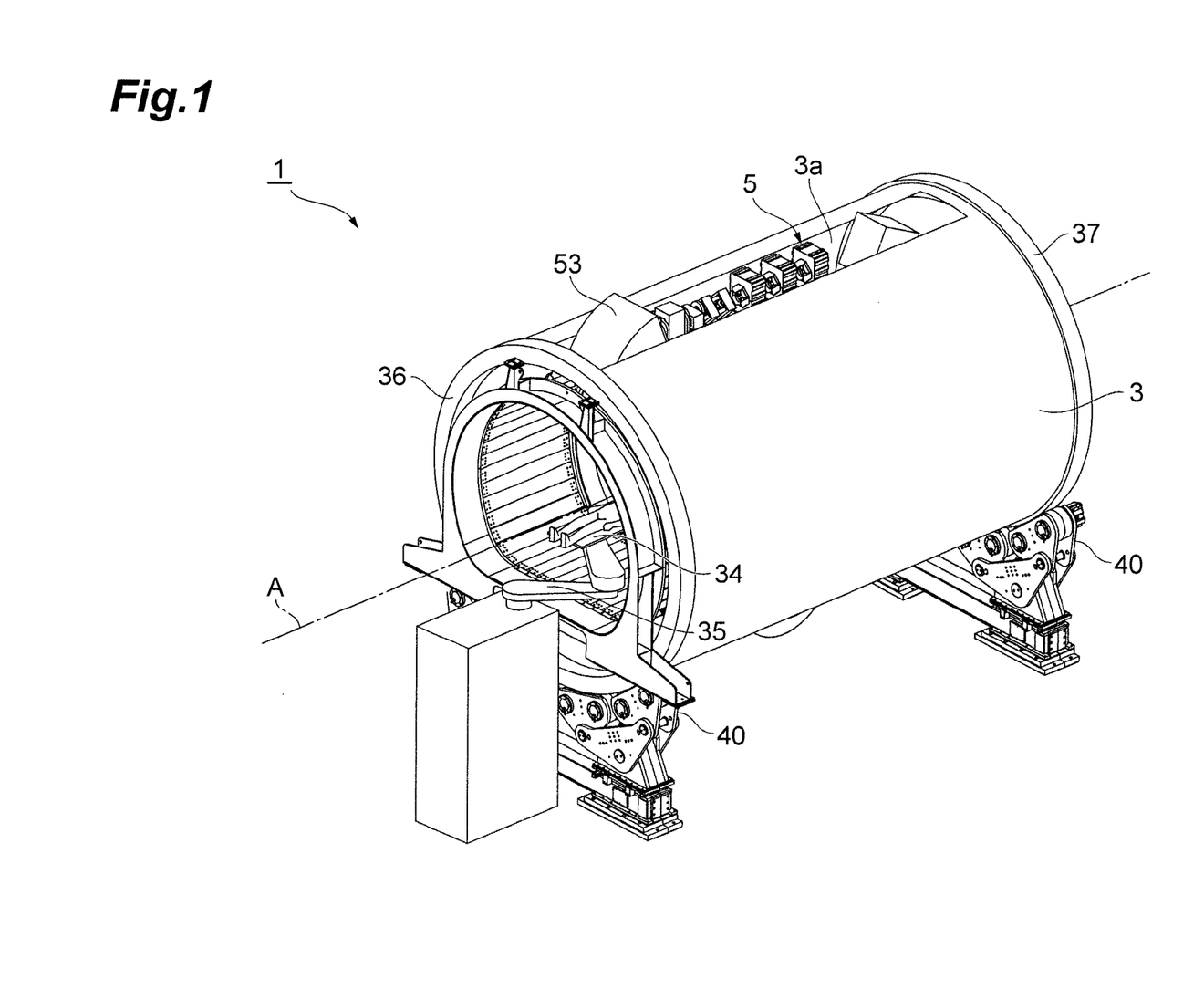
FIG. 1 is a perspective view showing a schematic overview of a proton therapy device (charged particle beam irradiation device) according to an embodiment of the present invention.
Figure 2:
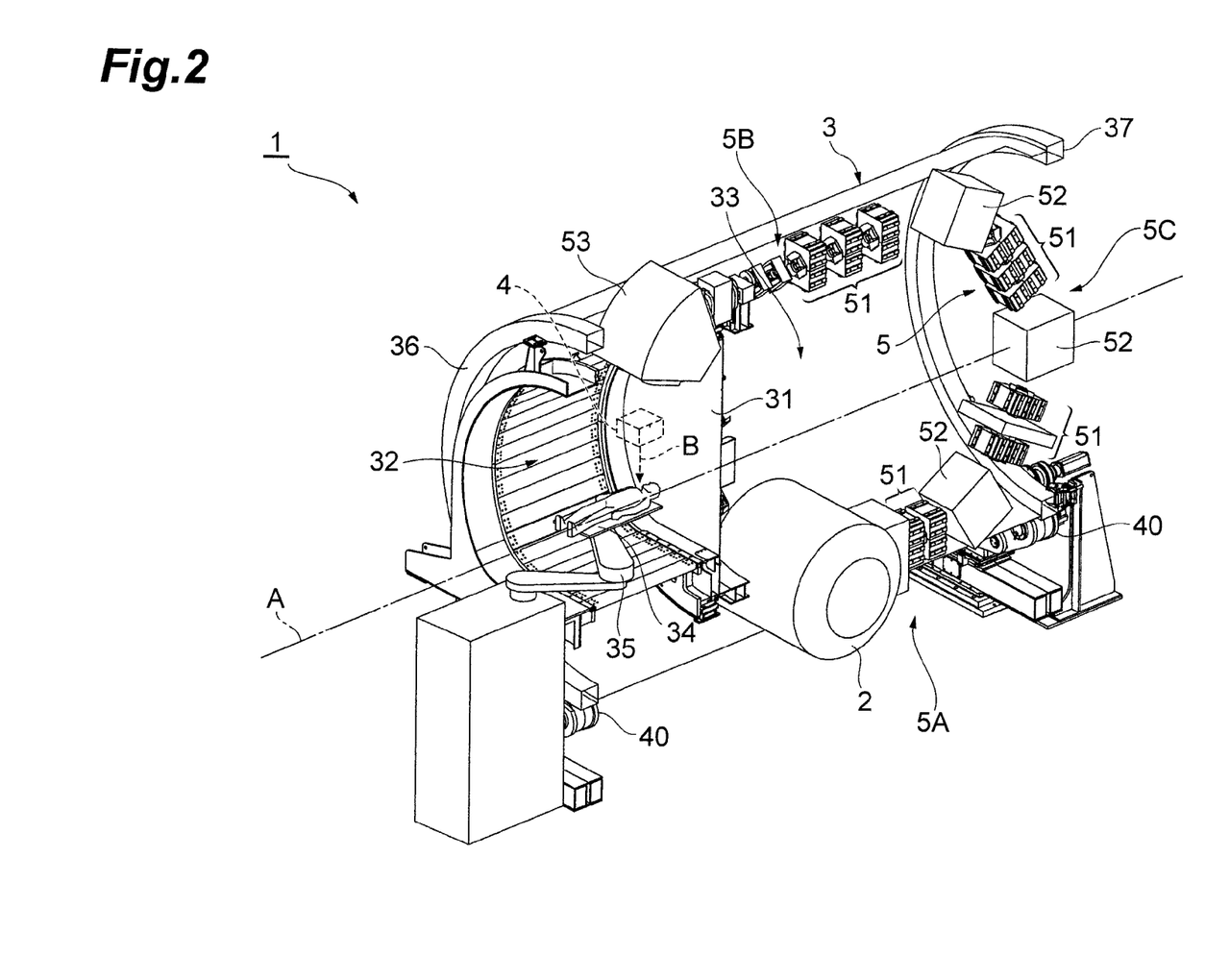
FIG. 2 is a partially sectioned perspective view in which half of a rotating part of FIG. 1 is cut away along the rotating axis of the rotating part.

First, with reference to FIGS. 1 and 2, a proton therapy device 1 according to a first embodiment of the present invention will be described. FIG. 1 is a perspective view showing a schematic overview of the proton therapy device 1 according to this embodiment. FIG. 2 is a partially sectioned perspective view in which half of a rotating part of FIG. 1 is cut away along the rotating axis of the rotating part.

As shown in FIGS. 1 and 2, the proton therapy device 1 includes a cyclotron (particle accelerator) 2 that accelerates ions (charged particles) generated by an ion source (not shown) and ejects a charged particle beam, a cylindrical outer shell part (rotatable gantry) 3 that is capable of rotating around a rotating axis, an irradiation nozzle (irradiation unit) 4 that is capable of irradiating an irradiation target with the charged particle beam, and a beam transport line 5 that transports the charged particle beam ejected from the cyclotron 2 to the irradiation nozzle 4.

The cyclotron 2 accelerates hydrogen ions supplied from the ion source (not shown), inside a vacuum chamber (not shown) and ejects a charged particle beam. The cyclotron 2 is connected to the beam transport line 5. The charged particle beam ejected from the cyclotron 2 is injected into the beam transport line 5.

As shown in FIGS. 1 and 2, the outer shell part 3 is a cylindrical body having a thin-wall structure and can be lightweight while maintaining rigidity. The outer shell part 3 is rotatably supported by roller devices 40, which are disposed below the outer shell part 3, around a cylindrical axis center A. The outer shell part 3 comes into contact with the roller devices 40 at cylindrical outer peripheral surfaces in the vicinity of both of the end portions. When the roller devices 40 are driven by a motor (not shown), a rotational force is applied to the outer shell part 3. Moreover, the rotation of the outer shell part 3 is stopped by a braking device (not shown). Furthermore, the entire length of the outer shell part 3 in the direction of the rotating axis A is, for example, 8 meters and the diameter thereof is, for example, 6 meters.

As shown in FIG. 2, the outer shell part 3 includes a partition plate 31 therein in such a manner that the partition plate 31 is substantially perpendicular to the rotating axis A. The inside of the outer shell part 3 is divided into two regions by the partition plate 31 in the direction of the rotating axis A. The two regions are a treatment region 32 that performs the irradiation of the charged particle beam and a proton beam generation region 33 that generates a proton beam.

A treatment table 34 on which a patient lies is disposed in the treatment region 32. The treatment table 34 is disposed in the vicinity of the rotating axis A of the outer shell part 3 by a moving unit (robot arm) 35 during the irradiation of the proton beam. The treatment table 34 can be moved between outside and inside (treatment region 32) of the proton therapy device 1 by using the moving unit 35 through the opening of the end portion 36 of the outer shell part 3 in the treatment region 32 side.

Furthermore, an irradiation nozzle 4 is fixedly disposed in the treatment region 32 of the outer shell part 3 to irradiate the proton beam in the direction B directed towards the rotating axis A of the outer shell part 3. The irradiation nozzle 4 freely revolves around the treatment table 34 in accordance with the rotation of the outer shell part 3. Therefore, the irradiation nozzle 4 can irradiate the patient on the treatment table 34 with the proton beam from an arbitrary direction around the rotating axis A of the outer shell part 3. In addition, the irradiation nozzle 4 is fixed to a bending magnet 53 described later, but may be fixed to the outer shell part 3 or the like. In other words, the irradiation nozzle 4 may be provided to rotate in accordance with the rotation of the outer shell part 3. Further, the irradiation nozzle 4 includes a scanning magnet that scans the proton beam in an X direction and a Y direction respectively perpendicular to the direction B. The proton beam can be irradiated onto the patient by the scanning method. Furthermore, a wobbler magnet may be provided in the irradiation nozzle 4. The proton beam may be irradiated onto the patient by the wobbler method.

The starting end of beam transport line 5 is connected to the cyclotron 2 and the finishing end thereof is connected to the irradiation nozzle 4. The beam transport line 5 transports the proton beam ejected from the cyclotron 2 to the irradiation nozzle 4. The beam transport line 5 includes a plurality of four-pole electromagnets 51 on which the proton beam is converged and a plurality of energy selection systems (ESS) 52 (three energy selection systems in FIG. 2) that take (select) the proton beam with a desired energy range (an energy range smaller than a predetermined energy range) out of the proton beams with the predetermined energy range. In addition, the beam transport line 5 includes the bending magnet (deflection magnet) 53 that deflects the proton beam (substantially 90 degrees in this embodiment) at a position immediately before the finishing end of the beam transport line 5 is connected to the irradiation nozzle 4 and that determines an incident direction of the proton beam to the irradiation nozzle 4. As shown in FIG. 2, in the treatment region 32, the bending magnet 53 is disposed in the centrifugal direction of the outer shell part 3 from the irradiation nozzle 4. A beam transport tube (not shown) is provided over the entirety of the beam transport line 5 along the trajectory of the proton beam. The inside of the beam transport tube is evacuated to suppress the scattering of the proton beam when the proton beam is transported through the beam transport tube.

Particularly, in this embodiment, the cylindrical outer shell part 3 functions as the outer shell of the entire proton therapy device 1 and can be lightweight while maintaining rigidity of the entire device. Moreover, the respective elements of the cyclotron 2 and the beam transport line 5 are at least partially housed within the outer shell part 3 and are held by the outer shell part 3. Here, specifically, "held by the outer shell part 3" means a state where the respective elements thereof are directly attached to the inside surface of the outer shell part 3 and a state where the respective elements thereof are connected to the inside surface of the outer shell part 3 through a member such as a bracket. Accordingly, in this configuration, the proton therapy device 1 of this embodiment has a compact structure in which all constituent elements related to the proton therapy are integrally assembled.

As shown in FIG. 2, the cyclotron 2 is held by the outer shell part 3 at a position facing the position of the finishing end of the beam transport line 5 (at least the bending magnet 53) around the rotating axis A of the outer shell part 3. In other words, the cyclotron 2 and the bending magnet 53 are respectively held by the outer shell part 3 at a position where the cyclotron 2 faces the bending magnet 53 centering on the rotating axis A at 180 degrees when seen from the view in parallel with the rotating axis A of the outer shell part 3, more specifically, at a position where the cyclotron 2 is positioned symmetrically with respect to the bending magnet 53 with the rotating axis A interposed therebetween when seen from the view in parallel with the rotating axis A.

As shown in FIG. 2, first, the beam transport line 5 extends towards the end portion 37 in the proton beam generation region 33 side (the direction opposite to the end portion 36 in the treatment region 32 side) from the starting end connected to the cyclotron 2, in parallel with the rotating axis A direction of the outer shell part 3 and along the inner peripheral surface of the outer shell part 3. Then, the beam transport line 5 passes through the rotating axis A of the outer shell part 3 in the vicinity of the end portion 37 inside the outer shell part 3, using three ESSs 52 and extends to the inner peripheral surface of the outer shell part 3 facing the position of the starting end thereof while being bent by 180 degrees. Finally, the beam transport line 5 extends to the bending magnet 53 of the treatment region 32 in parallel with the direction of the rotating axis A and along the inner peripheral surface of the outer shell part 3. In other words, the beam transport line 5 includes a first line 5A that extends from the starting end connected to the cyclotron 2 along the rotating axis A, a second line 5B that extends from the finishing end connected to the bending magnet 53 along the rotating axis A and a third line 5C that connects the first line 5A and the second line 5B.

That is, the respective elements of the cyclotron 2 and the beam transport line 5 are disposed on a virtual plane (corresponding to the cross-section of the outer shell part 3 in FIG. 2) extending in the diametrical direction of the cylindrical body along the rotating axis A of the outer shell part 3, in a substantially U-shaped manner.

In addition, the respective elements of the cyclotron 2 and the beam transport line 5 are held on the inside surface of the outer shell part 3. However, apart of the elements thereof may protrude to either side of the outer periphery of the outer shell part 3 to be exposed and the elements thereof may be disposed at least partially in the inner surface side of the outer shell part 3. For example, in the examples of FIGS. 1 and 2, the outer shell part 3 includes a rectangular cutout portion 3a that is open in an upper portion and extends along the beam transport line 5. Further, the four-pole electromagnets 51 and the bending magnet 53 are exposed through the cutout portion 3a, when seen from the outside of the outer shell part 3. As in this example, since a part of the cyclotron 2 and the beam transport line 5 is exposed on the outside of the outer shell part 3, it is possible to gain access to the cyclotron 2 and the beam transport line 5 from the outside of the outer shell part 3 through the cutout portion 3a, if necessary. Therefore, it is possible to perform maintenance on each part from the outside of the outer shell part 3, thereby improving maintainability.

In order that ions may be made to revolve in the vacuum chamber and be accelerated, the cyclotron 2 generally has a circular cylindrical shape having a central axis. As shown in FIG. 2, the cyclotron 2 may be disposed in such a manner that the central axis of the cyclotron 2 is perpendicular to the rotating axis A of the outer shell part 3 or in such a manner that the central axis thereof is parallel with the rotating axis A of the outer shell part 3. However, as shown in FIG. 2, when the cyclotron 2 is disposed in such a manner that the central axis of the cyclotron 2 is perpendicular to the rotating axis A of the outer shell part 3, the plane of the trajectory where the ions are accelerated in the cyclotron 2 is substantially equal to the plane of the beam transport line 5. Therefore, the charged particle beam can be easily taken out of the cyclotron 2.

In this proton therapy device 1, the cyclotron 2 and the beam transport line 5 may be at least partially housed within the cylindrical outer shell part 3. Accordingly, the constituent elements necessary for the irradiation of the proton beam (the cyclotron 2, the beam transport line 5 and the irradiation nozzle 4) are integrated into a whole, thereby miniaturizing the entire device. Further, since the entire proton therapy device 1 is integrally assembled, it is possible to assemble the proton therapy device 1 at a factory or the like in advance. Therefore, when the device is assembled at a factory or the like in advance, it is possible to shorten a process before a performance test at an installation location and to perform the performance test at the factory in advance. According to this, since the miniaturization of the device and the shortening of the installation process can be realized, it is possible to provide a greater range of choices for the installation location of the proton therapy device 1, thereby enhancing general versatility. Furthermore, since the entire proton therapy device 1 is covered with the cylindrical outer shell part 3, the proton therapy device 1 can be lightweight while maintaining rigidity. Since the proton therapy device 1 can maintain rigidity, it is possible to prevent the device from being bent, for example, due to the weight of the cyclotron 2 or the like. Therefore, it is possible to prevent occurrence of isocenter (an intersection point between the rotating axis A and the center line of the proton beam) displacement in the irradiation nozzle 4, thereby improving the irradiation accuracy of the proton beam.

Generally, the bending magnet 53, which determines an incident direction in the finishing end of the beam transport line 5, is large-size and the weight thereof is high, for example, the weight thereof is approximately 20 to 25 tons. Moreover, the cyclotron 2 has approximately the same weight as the bending magnet 53. Here, in this embodiment, the cyclotron 2 and the bending magnet 53 of a finishing end of the bending magnet 53 are respectively held at a position where the cyclotron 2 faces the bending magnet 53 around the rotating axis A of the outer shell part 3. Therefore, elements having approximately the same weight may be disposed in such a manner that the elements face each other around the rotating axis A, thereby improving balance around the rotating axis A of the outer shell part 3. In addition, the cyclotron 2 and the bending magnet 53, which are held at a position where the cyclotron 2 faces the bending magnet 53 around the rotating axis A, function as each other's counterweight. Therefore, it is not necessary to provide a new counterweight, thereby realizing the lightweight device.

The respective elements of the cyclotron 2 and the beam transport line 5 are held on the inner peripheral surface of the outer shell part 3. In this configuration, the constituent elements necessary for the irradiation of the proton beam, that is, the cyclotron 2, the beam transport line 5 and the irradiation nozzle 4 are disposed inside the outer shell part 3. Accordingly, it is possible to perform maintenance and adjustment on the constituent elements from the inside of the outer shell part 3, thereby improving work efficiency of the maintenance.

Since the energy selection systems 52 do not protrude in the direction of the rotating axis A of the outer shell part 3 and the energy selection systems 52 are housed within the outer shell part 3, the entire device can be further miniaturized. In addition, when the proton therapy device 1 assembled at a factory or the like is transported to an installation location, the outer shell part 3 may protect the energy selection systems 52. Therefore, it is possible to prevent the energy selection systems 52 from being damaged when hitting against another object.

The beam transport line 5 includes the first line 5A that extends from the starting end along the rotating axis A, the second line 5B that extends from the finishing end along the rotating axis A and the third line 5C that connects the first line 5A and the second line 5B. Therefore, it is possible to increase the deflection angle of the proton beam by the beam transport line 5. Accordingly, since the plurality of the energy selection systems 52 are disposed in the beam transport line 5 having a large deflection angle, it is possible to select energy of the proton beam in a stepwise manner, thereby selecting energy with high accuracy.

Second Embodiment

Figure 3:
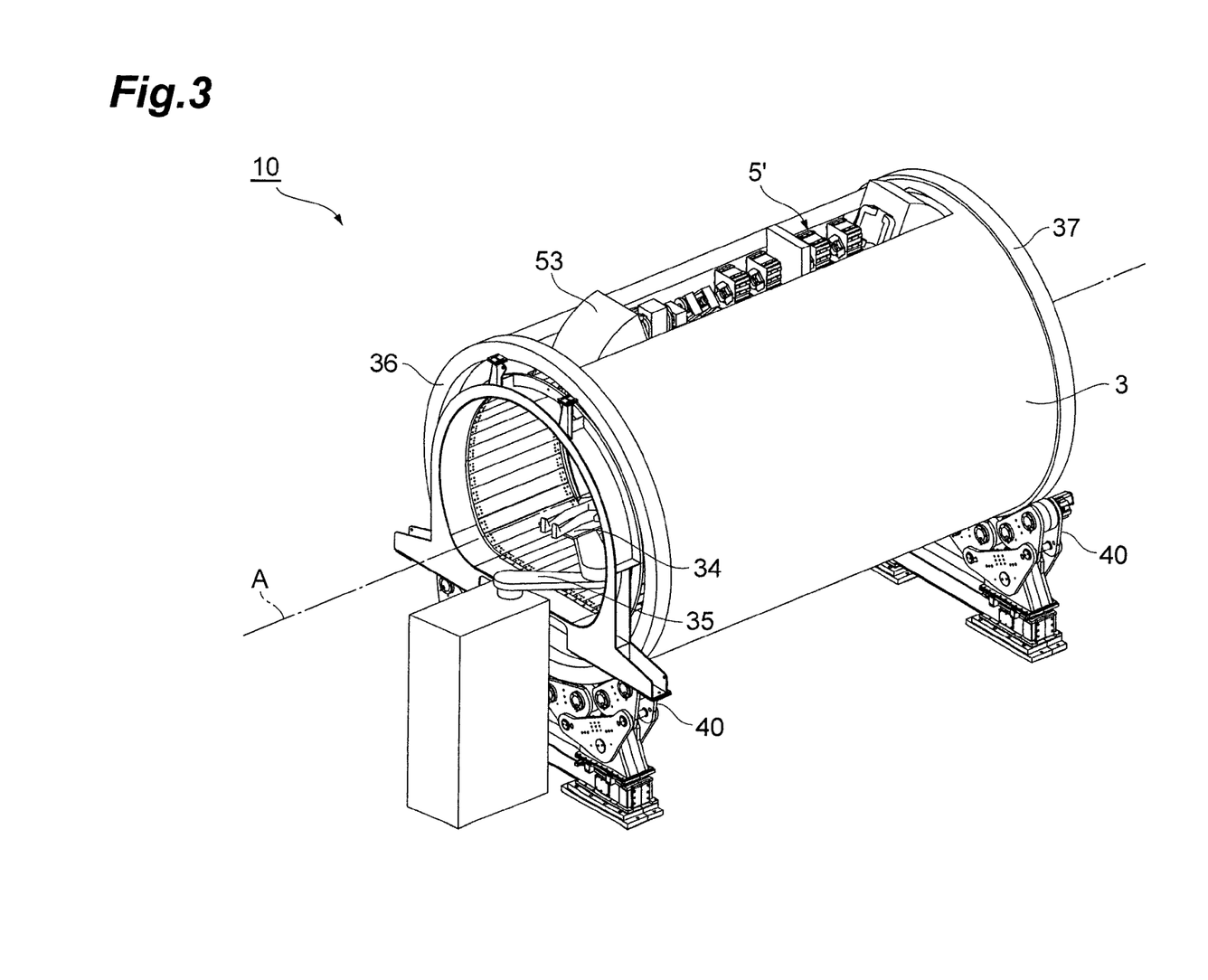
FIG. 3 is a perspective view showing a schematic overview of a proton therapy device according to another embodiment of the present invention.
Figure 4:
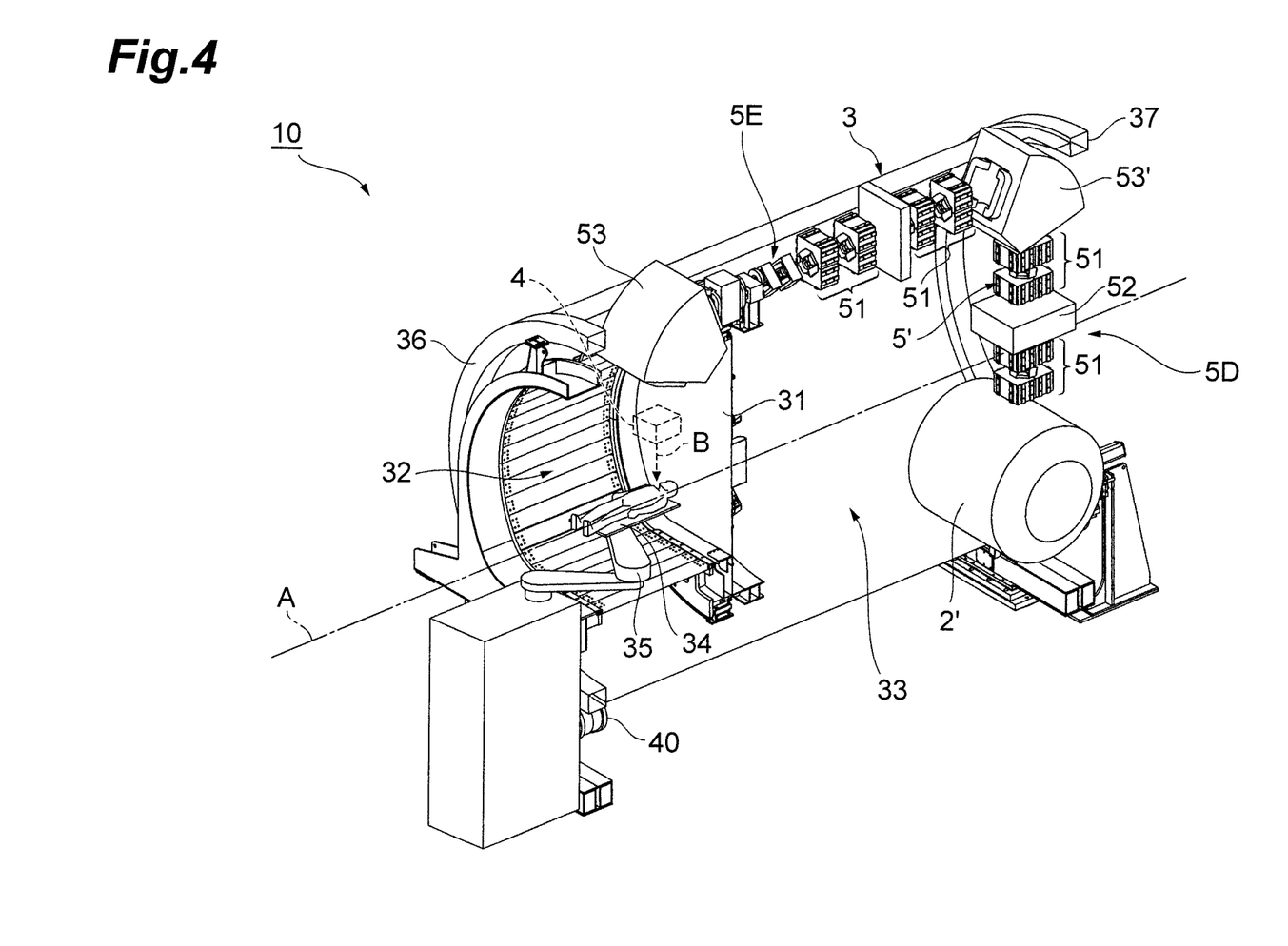
FIG. 4 is a partially sectioned perspective view in which half of a rotating part of FIG. 3 is cut away along the rotating axis of the rotating part.

With reference to FIGS. 3 and 4, a proton therapy device 10 according to a second embodiment of the present invention will be described. FIG. 3 is a perspective view showing a schematic overview of the proton therapy device 10 according to this embodiment. FIG. 4 is a partially sectioned perspective view in which half of a rotating part of FIG. 3 is cut away along the rotating axis of the rotating part.

The proton therapy device 10 according to the second embodiment is different from the proton therapy device 1 according to the first embodiment in that (1) a cyclotron 2' is disposed in the vicinity of the end portion 37 of the outer shell part 3 in the proton beam generation region 33 side and (2) the arrangement of a beam transport line 5' is substantially L-shaped in accordance with the installation location change of the cyclotron 2'.

As shown in FIG. 4, the cyclotron 2' is held by the outer shell part 3 at a position facing the position of the finishing end of the beam transport line 5' (at least the bending magnet 53) around the rotating axis A of the outer shell part 3, and in the end portion (the other end portion) 37 side of the outer shell part 3 in the proton beam generation region 33 side. On the other hand, as shown in FIGS. 3 and 4, the bending magnet 53 is held by the outer shell part 3 in the end portion (one end portion) 36 side of the outer shell part 3 in the treatment region 32 side. That is to say, the cyclotron 2' and the bending magnet 53 are respectively disposed in the outer shell part 3 at positions in the vicinity of both end portions 36 and 37 of the outer shell part 3. The cyclotron 2' and the bending magnet 53 are respectively held by the outer shell part 3 at a position where the cyclotron 2' is positioned antisymmetrically with respect to the bending magnet 53 with the rotating axis A interposed therebetween.

As shown in FIG. 4, from the starting end connected to the cyclotron 2', first, the beam transport line 5' passes through the two sets of four-pole electromagnets 51 in the vicinity of the end portion 37 inside the outer shell part 3 to the rotating axis A of the outer shell part 3 and then extends in the direction perpendicular to the rotating axis A toward the upper portion of the inner peripheral surface of the outer shell part 3 that faces the position of the starting end. Then, the beam transport line 5' is bent by using the bending magnet 53' by 90 degrees in the direction in parallel with the rotating axis A and extends to the bending magnet 53 in the treatment region 32 along the inner peripheral surface of the outer shell part 3. In other words, the beam transport line 5' includes a fourth line 5D that extends from the starting end connected to the cyclotron 2' in the direction perpendicular to the rotating axis A and a fifth line 5E that extends from the finishing end connected to the bending magnet 53 along the rotating axis A.

That is to say, the respective elements of the cyclotron 2' and the beam transport line 5' are disposed on a virtual plane (corresponding to the cross-section of the outer shell part 3 in FIG. 4) extending in the diametrical direction of the cylindrical body along the rotating axis A of the outer shell part 3, in a substantially L-shaped manner.

According to the proton therapy device 10, the bending magnet 53 is held at the position of one end portion 36 side in the direction along the rotating axis A of the outer shell part 3 and the cyclotron 2' is held at the position of the other end portion 37 side in the direction along the rotating axis A of the outer shell part 3. Therefore, it is possible to improve balance of the outer shell part 3 in the direction of the rotating axis A and to reduce the bending of the direction of the rotating axis A of the proton therapy device 10. Moreover, since the proton therapy device 10 has the same configuration as the proton therapy device 1 according to the first embodiment, the proton therapy device 10 has the same functional effect as the above-described proton therapy device 1.

In the proton therapy device 10, the beam transport line 5' includes the fourth line 5D that extends from the starting end in the direction perpendicular to the rotating axis A and the fifth line 5E that extends from the finishing end along the rotating axis A. That is, unlike the proton therapy device 1 according to the first embodiment, the beam transport line 5' is bent in such a manner that the trajectory of the proton beam is bent by only approximately 90 degrees (in the first embodiment, bent by 180 degrees). According to this, it is possible to omit the length in the direction of the rotating axis A necessary for bending the third line 5C in the first embodiment, thereby shortening the entire length of the beam transport line 5' in the direction of the rotating axis A. Consequently, since the entire length of the outer shell part 3 in the direction of the rotating axis A can be shortened, the proton therapy device 10 according to the second embodiment can be miniaturized to a greater extent than the proton therapy device 1 according to the first embodiment.

Hereinbefore, the embodiments of the present invention were described in detail, but the present invention is not limited to the above-described embodiments. For example, the arrangements or the numbers of the respective elements configuring the beam transport lines 5 and 5' according to the first and second embodiments may be appropriately changed depending on design of a desired beam.

The particle accelerator may not be limited to the cyclotron, but may be a synchrotron or a synchrocyclotron. When a superconducting particle accelerator is used, the proton therapy device 1 may be further miniaturized. Further, the charged particle beam may not be limited to the proton beam, but may be a carbon ion beam (heavy particle beam). Furthermore, the shape of the outer shell part 3 may not be limited to a cylindrical shape, but may be another tubular shape.

The outer shell part 3 may not be limited to rotate by 360 degrees, but may rotate (oscillate) less than 360 degrees (for example, 180 degrees).

According to the embodiments of the present invention, it is possible to miniaturize the entire charged particle beam irradiation device and to shorten an installation process of the charged particle beam irradiation device.

It should be understood that the invention is not limited to the above-described embodiment, but may be modified into various forms on the basis of the spirit of the present invention. Additionally, the modifications are included in the scope of the invention.

What is claimed is:

1. A charged particle beam irradiation device comprising:
    a particle accelerator configured to accelerate charged particles and to eject charged particle beam;
    an outer shell part that is cylindrical and configured to rotate around a rotating axis;
    an irradiation unit configured to irradiate an irradiation target with the charged particle beam, the irradiation direction of which changes in accordance with the rotation of the outer shell part; and
    a beam transport line configured to transport the charged particle beam ejected from the particle accelerator to the irradiation unit, wherein the particle accelerator and the beam transport line are each at least partially housed within the outer shell part.

2. The charged particle beam irradiation device according to claim 1,
    wherein the particle accelerator and the beam transport line are held on an inner peripheral surface of the outer shell part.

3. The charged particle beam irradiation device according to claim 1 or 2,
    wherein the beam transport line includes an energy selection system that takes the charged particle beam having an energy range smaller than a predetermined energy range out of the charged particle beams having the predetermined energy range, and
    wherein the energy selection system is housed within the outer shell part.

4. The charged particle beam irradiation device according to claim 1 or 2,
    wherein the outer shell part includes a cutout portion, and
    wherein the particle accelerator and the beam transport line are at least partially exposed through the cutout portion.

5. The charged particle beam irradiation device according to claim 1 or 2,
    wherein the beam transport line includes a deflection magnet, which determines an incident direction to the irradiation unit, at a finishing end of the beam transport line, and
    wherein the particle accelerator and the deflection magnet are respectively held at a position where the particle accelerator faces the deflection magnet around the rotating axis when seen from the view in parallel with the rotating axis.

6. The charged particle beam irradiation device according to claim 5,
    wherein the beam transport line includes a first line that extends from a starting end of the beam transport line connected to the particle accelerator along the rotating axis, a second line that extends from the finishing end of the beam transport line along the rotating axis and a third line that connects the first line and the second line.

7. The charged particle beam irradiation device according to claim 5,
    wherein the deflection magnet is held at a position of one end portion side in the direction along the rotating axis of the outer shell part, and wherein the particle accelerator is held at a position of the other end portion side in the direction along the rotating axis of the outer shell part.

8. The charged particle beam irradiation device according to claim 7,
wherein the beam transport line includes a fourth line that extends from a starting end of the beam transport line connected to the particle accelerator in the direction perpendicular to the rotating axis and a fifth line that extends from the finishing end of the beam transport line along the rotating axis.

* * * * *